United States Patent [19]

Sargent

[11] Patent Number: 4,754,511
[45] Date of Patent: Jul. 5, 1988

[54] SUPPORT CUSHIONS

[75] Inventor: Clement D. Sargent, Rye, N.Y.

[73] Assignee: Theracom Corporation, Rye, N.Y.

[21] Appl. No.: 32,220

[22] Filed: Mar. 31, 1987

Related U.S. Application Data

[63] Continuation-in-part of Ser. No. 866,020, May 21, 1986, Pat. No. 4,675,930, and a continuation of Ser. No. 026,349, Mar. 16, 1987.

[51] Int. Cl.⁴ .............................................. A47C 27/08
[52] U.S. Cl. ........................................... 5/449; 5/431; 5/441; 5/446
[58] Field of Search ................... 5/441, 449, 455, 457, 5/458, 450, 465, 448, 431, 481, 446, 447

[56] References Cited

U.S. PATENT DOCUMENTS

| | | | |
|---|---|---|---|
| 379,827 | 3/1888 | Snavely et al. | 5/458 |
| 2,360,715 | 10/1944 | Perry | 5/458 |
| 2,390,955 | 12/1945 | McDonnell | 5/458 |
| 2,655,369 | 10/1953 | Musilli | 5/458 |
| 2,982,341 | 5/1961 | Bisser | 5/458 |
| 3,205,106 | 9/1965 | Cross | 5/458 |
| 3,574,397 | 4/1971 | Norriss | 297/391 |
| 3,899,210 | 8/1975 | Samhammer et al. | 5/481 |
| 3,899,797 | 8/1975 | Gunst | 5/458 |
| 4,011,611 | 3/1977 | Lederman | 297/456 |
| 4,021,871 | 5/1977 | Wortman | 5/434 |
| 4,027,888 | 6/1977 | Wilcox | 297/284 |
| 4,031,578 | 6/1977 | Sweeney et al. | 5/337 |
| 4,139,920 | 2/1979 | Evans | 5/455 |
| 4,218,792 | 8/1980 | Kogan | 5/436 |
| 4,320,543 | 3/1982 | Dixon | 5/434 |
| 4,324,012 | 4/1982 | Cannaday | 5/432 |
| 4,328,599 | 5/1982 | Mollura | 5/458 |
| 4,513,452 | 4/1985 | Thomas | 5/442 |
| 4,535,495 | 8/1985 | Oldfield | 5/432 |
| 4,550,459 | 11/1985 | Endel et al. | 5/437 |
| 4,607,403 | 8/1986 | Alivizatos | 5/449 |

Primary Examiner—Alexander Grosz
Attorney, Agent, or Firm—Pennie & Edmonds

[57] ABSTRACT

A cushioning apparatus having exterior surface means which form a desired shape and define an internal cavity therein, and a plurality of spherical pellets which substantially fill the internal cavity. External prestressing means, internal tension members, nonstretchable panels, or an adjustable draw cord may be utilized for guiding, maintaining or changing the shape and firmness of certain sizes or configurations. The apparatus may be easily conformed to a desired shape by the user for support of a body member or the like.

23 Claims, 3 Drawing Sheets

SUPPORT CUSHIONS

CROSS REFERENCE TO RELATED APPLICATIONS

This application is a continuation-in-part of application Ser. No. 866,020, filed 5/21/86, now issued as U.S. Pat. No.4,675,930 on June 30, 1987, and a continuation of design application Ser. No. 026,349, filed Mar. 16, 1987.

TECHNICAL FIELD

The invention relates to cushions or cushioning devices and specifically to a cushion or pillow which can be easily shaped to conform to a body member for orthopedic support.

BACKGROUND ART

Various cushioning devices or pillows have been developed whereby the shape of the pillow is designed to provide support for a body member of the user. Typical examples of such pillows or cushions can be found in U.S. Pat. Nos. 5,513,462 (neck support); 3,574,397 (head support); 4,324,012 and 4,535,495 (back support); and 4,031,578, 4,218,792, 4,320,543 and 4,550,459 (head and neck support). To provide such support, these cushions were constructed and designed to conform the shape of the body part to be supported.

Conventional pillows are usually filled with a cushioning material of cotton, feathers, sponge rubber, fiberfill and/or foam. The sponge or foam fillers may be in the form of chunks or particles. Such pillows can be manipulated to conform to the shape of the body part to be supported. If the construction of the pillow is too stiff, however, it becomes difficult to conform the shape of the pillow to the body part. Conversely, if the pillow is too soft, depressions are easily formed, and the proper support of the body member is not achieved. Furthermore, the shaping capabilities of such conventional pillows are rather limited. Often, the filler simply packs into a dense mass and loses it resiliency.

U.S. Pat. No. 4,021,871 discloses an improvement on the previous devices in that the internal cavity of the cushion is filled with a layer of fibrous textile filler positioned in a particular manner to provide a cushion which retains its shape more effectively and imparts improved cushioning resistance.

None of these prior art cushioning devices is capable, however, of being easily shaped to the desired configuration to provide support, while retaining sufficient resiliency to maintain the desired shape until it is changed by the user. Furthermore, if the pillow cannot be conformed the exact shape needed for support, the user can feel displeasure, discomfort, or pain.

SUMMARY OF THE INVENTION

The present invention relates to a lightweight shapable cushioning apparatus which is easily conformable to a desired configuration for supporting an item comprising exterior surface means of a material stretchable in two directions forming a desired shape for the apparatus and defining an internal cavity therein, and a plurality of lightweight, resilient, solid, expanded thermoplastic spheres substantially filling the internal cavity. The spheres are capable of compression, deformation and three-dimensional movement throughout the internal cavity to allow shaping of the apparatus for support of an item. The spheres are further capable of returning to their spherical shape after the item to be supported is removed from the apparatus. For certain apparatus, external prestressing means may be used to control the shape of the apparatus.

The exterior surface means may be made of any natural or synthetic fabric, preferably a stretch fabric of a lightweight, stretchable synthetic material while the spheres are preferably made of a thermoplastic or expanded thermoplastic material.

An alternate embodiment of the invention relates to the lightweight cushioning apparatus described above along with means for adjusting the shape of the apparatus. One adjusting means includes draw cord means extending through the internal cavity. If desired, locking means can be utilized with the draw cord means for retaining the adjusted shape of the apparatus. Alternately a portion of the exterior surface means may be made of a non-stretchable material to assist in holding or guiding the reshaping during adjustment, thus maintaining the shape of the apparatus.

A further embodiment of the invention relates to a lightweight cushioning apparatus described above which further includes internal or external frame means for forming a desired shape for the apparatus or for holding it erect. It is also possible to include means for bending the article about a predetermined curved or straight line for folding or bending the article. Such bending means may include a plurality of tension cords aligned along the predetermined line. Alternately, a seam or panel of non-stretchable fabric can be used.

BRIEF DESCRIPTION OF THE DRAWINGS

The nature, advantages, and various other additional features of the invention will appear more fully upon consideration of the illustrative embodiments now to be described in detail in connection with the accompanying drawing figures, wherein.

DETAILED DESCRIPTION OF THE PREFERRED EMBODIMENTS

Referring initially to FIGS. 1-4, there is illustrated a support cushion 10 in the form of a back rest for a chair or automobile seat. The exterior covering 20 of the cushion 10 can be made of any of a variety of natural or synthetic cloth or fabric materials. Preferably, the covering 20 is made of a synthetic, elastic or stretch fabric, whether woven or knitted. It has been found that synthetic polyester materials having good stretchability, preferably in both the X and Y directions (i.e., 2-way stretch materials), with stretch retention, washability and non-allergenic properties are preferred. The optimum material for such pillows is available from Dupont under the trade name Lycra Spandex. This material can be combined with other fibers (cotton, nylon, etc.) to produce fabrics of varying weights and stretch factors which could be selected depending upon the desired end use for the cushion.

Figure 3:
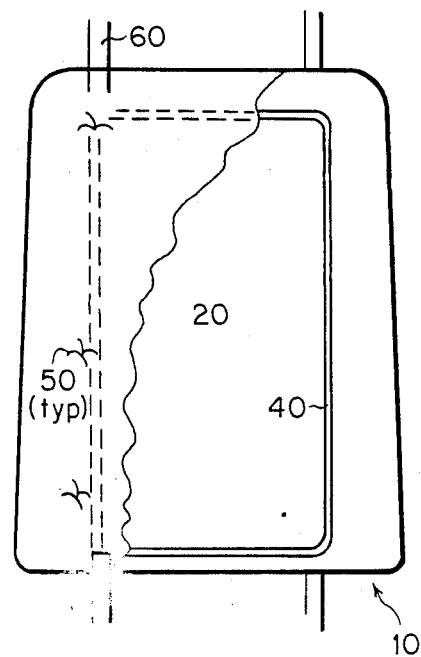
FIG. 3 is a rear plan view, partially in cross-section, of the support cushion of FIG. 1.
Figure 4:
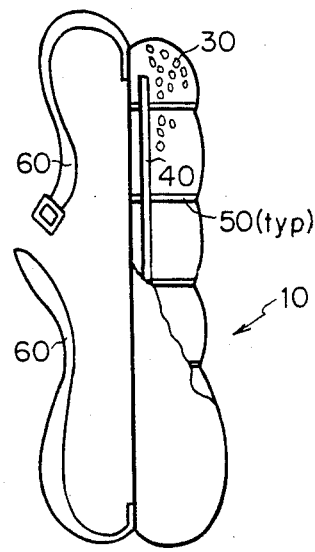
FIG. 4 is a side plan view, partially in cross-section, of the support cushion of FIG. 1.
Figure 2:
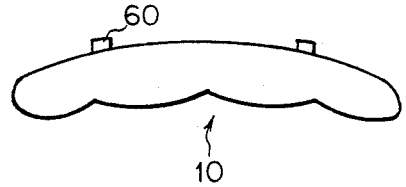
FIG. 2 is a top plan view of the support cushion of FIG. 1.

FIG. 4 illustrates the cushion with a portion of the side panel removed to detail the spherical plastic foam spheres 30 and wire frame 40 which are located inside. Tension members 50 are used to pre-stress opposed faces of the exterior covering 20 while the spheres 30 prevent the opposed faces the exterior covering from being drawn together. Also, the frame 40 enables the cushion to initially conform to the desired shape, i.e., that of a seat back for the cushion of FIGS. 1–4. Straps 60 are used to mount cushion 10 upon a chair or automobile seat.

The wire frame 40 can also be made with graphite or high strength plastic rods, and is used to provide stiffness to the pillow as well as to offset a certain degree of manipulation of the pillow beyond a particular shape. Thus, the pillow can be conformed to the support upon which it is attached but the user will not be able to deform it to an unusable or uncomfortable shape.

A wide variety of plastic or elastomeric foam particles or pellets are available at present and any of the generally known types are suitable for use in one embodiment of this invention. Again, for the construction of a lightweight pillow, the low density foamed materials, such as foamed or expanded polyethylene, polypropylene, polystyrene and the like, are preferred. All of the pellets used in this invention, however, should be resilient, washable, and capable of retaining their resiliency over an extended period of use and time. The smaller size pellets generally contribute to a soft cushion which can be easily manipulated to conform to a particular or desired shape, while the larger pellets produce a somewhat firmer cushion. Also, a wide range of pellet sizes can be used in the cushion without departing from the invention.

The preferred pellets for use in constructing the lightweight cushions of the present invention include any foam or expanded plastic materials in the form of spheres. The size range for such spheres is not essential to the use of the support cushion. However, it is preferred that a majority of the spheres used in the apparatus have diameters between 1/64 and ½ inch; most preferably between 1/32 and ¼ inch. Preferred materials would again included expanded thermoplastic foams, with expanded polystyrene foam spheres being the most advantageous from the standpoint of light weight. When the pillow is filled with particles of substantially uniform diameters on the order of ¼ inch or greater, a relatively firm cushion is provided. For softer and more easily shapable cushions, it is preferred to use spheres having diameters in the range between ¼ and ⅛ inch or smaller. Particle sizes having a diameter above ½ inch are generally selected for very large cushions or mattresses which in turn may be necessary for supporting the user's entire body, or for larger objects, such as animals. Again, as noted above, different size pellets may be used to obtain cushions having the desired softness or firmness for the particular application, and commercially available spheres usually include a variety of different diameters.

Expanded or foamed thermoplastics are preferred due to their springiness, resiliency, and ultra-light weight. If spheres of these materials are compressed, they will substantially return to their original shape after the compressive force has been removed. Thus, the spheres contribute to the invention in that they are easily capable of movement or deformation to allow shaping of the cushion. If they are deformed, these spheres do return to their original configuration reasonably well after the item to be supported is removed from the pillow. This also enables the cushion to be easily shaped, since the spheres can easily be moved through the internal cavity without interference from the tension elements or draw-cord. In addition, the use of such expanded thermoplastics in conjunction with lightweight covering materials enables an extremely ultra lightweight overall cushion to be provided. For example, a 14"×10"×10" box-like cushion containing expanded polystyrene spheres having diameters between ⅛ and ¼ inch with a Lycra Spandex fiber blend of 40.8% cotton, 35.4% Lycra, and 23.8% nylon as the outer surface material and Lycra Spandex tension members would weigh approximately 13½ ounces. This is a significant improvement in weight compared to the much heavier pillows of the prior art.

Figure 1:
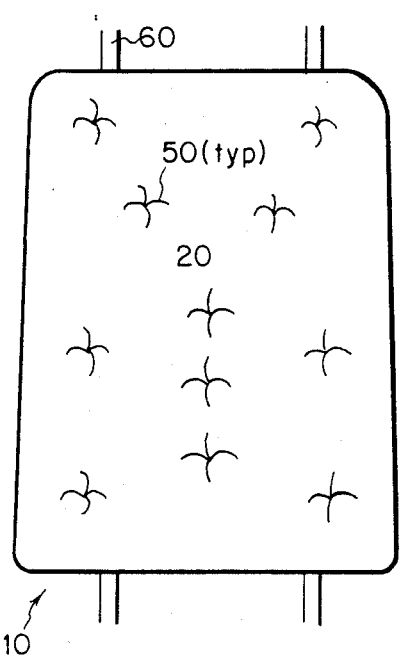
FIG. 1 is a front plan view of an orthopedic backrest support cushion.

As is evident from FIGS. 1 and 3, the opposed exterior surfaces 20 of the cushion 10 are pre-stressed by connecting thereto a plurality of tension members 50 in the form of elastic cord or other similar flexible connectors. Such flexible connectors can be in the form of fiber, tube, rod, bar, strip or the like: the only requirement being that they have a flexible or elastic nature which when at rest can be extended or stretched and which when stretched attempts to return to its rest position. When the user attempts to conform the cushion to a particular shape to comfortably fit the shape of the user's back, the elastic tension members 50 are allowed to expand and contract, thus facilitating the shaping of the cushion 10 and also maintaining the cushion in the desired shape until it is later changed to a different shape by the user.

A preferred material for these tension members is also the Lycra Spandex material referred to above. Similar materials having the ability to stretch and contract numerous times, while also being washable without losing its flexibility over time, can also be used. Various thermoplastics or elastomeric materials, including natural or synthetic latexes, are suitable for these tension members. Generally, while the solid or hollow diameter tube or rod is preferred, it is also possible to use rectangular or square cross-sectional hollow or solid bar materials or even fabric of various widths. When fabric is used, the width of the material would generally be on the order of about ¼ to ½ inch. Larger width material may be used for larger sized cushions or where additional tension force is required, provided that the movement of the thermoplastic spheres is not substantially restricted.

The tension members are generally spaced on 4 to 5 inch centers across the exterior surface 20 of the cushion 10. The pattern of a spaced elastic cord attachment positions can be square, diamond shaped, centered or off-centered. The 4 to 5 inch spacing is not critical and again would be determined by the size of the cushion. Tension member spacings smaller than about 1 inch generally provide an excessive number of such members, whereas spacing of greater than 10 inches is usually insufficient to prestress the opposed surfaces, particularly in larger size cushions. These members may be parallel or they may cross each other at an angle, depending on the size (i.e. shape, length, width and/or depth) of the cushion. The arrangement and spacing of the tension members (or tufts) is determined by the specific support needs. Those skilled in the art can best determine the preferred arrangement of these members to obtain the results desired.

When the tension cords are attached, they are stretched and pulled relatively taut so that the outer surfaces of the pillow are maintained under tension in a pre-stressed condition. This is shown in the FIGS. as an indentation in the surface of the exterior cover. Although each point of attachment (i.e., indentation) normally utilizes a single tension member, it may be desirable to use two or more smaller size tension members at each indentation. This is particularly useful in large pillows where single tension members would have to be relatively large. The filling of the pillow with the expanded thermoplastic spheres thus enables the cushion to maintain its normal exterior shape (i.e. round, square, rectangular, wedge etc.).

Figure 5:
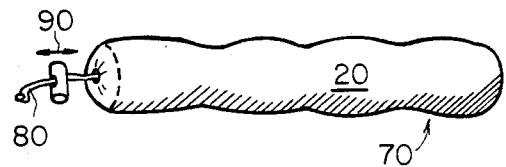
FIG. 5 is a perspective view of a travel support cushion in an elongated position.
Figure 6:
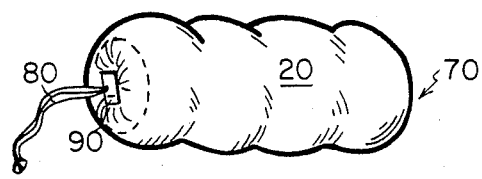
FIG. 6 is a perspective view of the support cushion of FIG. 5 in a compact position.
Figure 8:
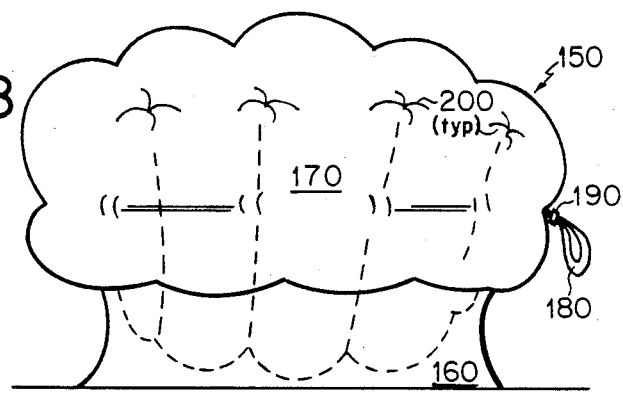
FIG. 8 is a side view of a support cushion in accordance with the teachings of the invention placed in a support ring to form a chair.

FIGS. 5 and 6 illustrate additional embodiments of support cushions according to the invention. There, an elongated pillow 70 having exterior surface means 20 containing a plurality of the thermoplastic spheres are used. A draw cord 80 and an appropriately located locking nut 90 are used to form either a thin elongated pillow, with the locking nut at a retracted position as shown in FIG. 5, or short, stubby pillow, with the locking nut compressing the pillow as shown in FIG. 6. The draw cord 80 is attached to one end of the pillow 70, passes through the internal cavity, and exits the opposite side of the pillow through the surface means 20. In other embodiments of the invention using a draw cord, such as shown in FIG. 8, the draw cord 80 can pass through the surface means in multiple locations. The light weight and shapeability of the cushion 70 in conjunction with the draw cord 80, enables a wide range of shapes and "hardness" (or compactness) of the spheres to suit the desire of the user.

Also, exterior prestressing means (not shown), again in the form of tension cord but this time wrapped around the circumference of exterior surface 20, can be used to help hold the pillow in the shape formed by the user. The desired configuration of the particular pillow to be manufactured will determine whether such exterior prestressing means are necessary, with elongated pillows not having a draw cord generally requiring the additional prestressing means.

Figure 7:
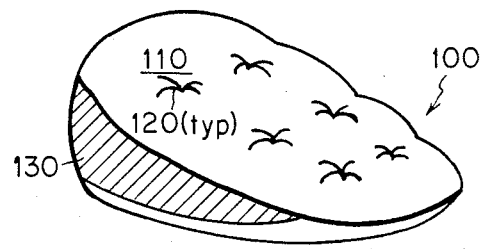
FIG. 7 is a perspective view of a maternity support cushion.

Referring now to FIG. 7 there is illustrated a support cushion 100 formed of exterior surface means 110 of the type described above and also having a plurality of tension cords shown as indentations 120. The shape of the pillow 100 is further defined by use of non-stretch fabric 130 for a portion of the exterior surface means. In certain situations, the use of the non-stretchable fabric 130 enables the tension cords 120 to be eliminated or only necessary on certain faces, while more versatile pillows can be made by using a combination of the non-stretchable fabric 130 and tension cords 120. Preferred non-stretchable fabrics for the panel 130 include cotton, suede, denim, nylon, corduroy, and the like. Furthermore, draw cord and locking means as disclosed in FIGS. 5 and 6 can be used to provide further shapeability and forming configurations of the pillow 100. Instead of non-stretchable fabric, non-stretchable or surgical tape can be used to maintain a desired shape for the pillow.

FIG. 8 shows a seating apparatus 150 comprised of a support element 160 and a cushion 170. As shown in FIG. 8, both draw cord 180, locking means 190, and tension cords 200 are used to assist in the shaping of the cushion 170 with the support element 160 assisting in the possible configurations attainable by the apparatus. Support ring 160, preferably made of metal or plastic, is used to hold the cushion in a predetermined manner so that it can be used as a footstool, chair, hassock or the like. The shape of the cushion 150 can be varied by the use of the draw cord 180 as well by manipulation of the tension cords 200 by compression from the user.

Figure 11:
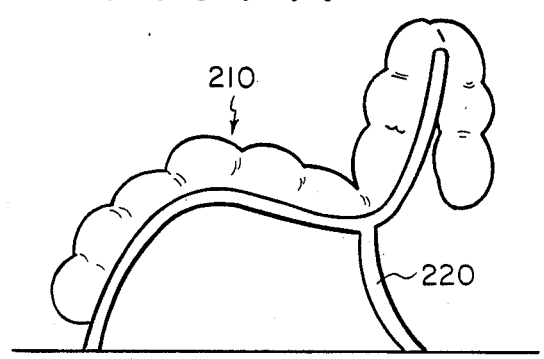
FIG. 11 is a side view of the cushion of FIG. 10 placed upon a support element.

Other cushion supports are shown in FIGS. 8 and 11. This allows a certain degree of shaping of the cushions within the original support so that the user can experience the desire degree of comfort while not manipulating the cushion to an unuseable configuration.

Figure 9:
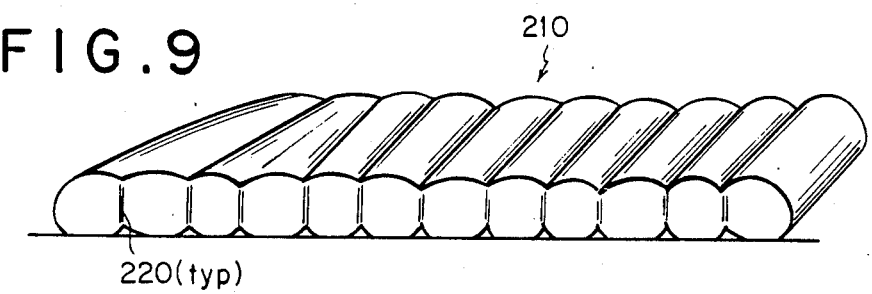
FIG. 9 is an embodiment of a support cushion in the form of a mattress.
Figure 10:
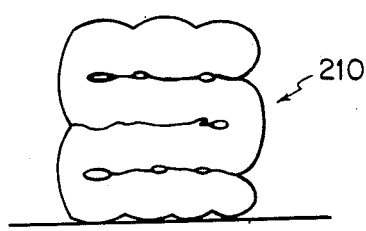
FIG. 10 is a side view of the cushion of FIG. 9 in a folded or chair configuration.

FIG. 9 shows a support cushion in the form of a mattress 210 having a plurality of tension cords 220 which are aligned along the width of the mattress space in rows or arrays. In order to accommodate folding of the mattress into segments, certain rows of tension cords are aligned so that a hinge will be created. This can be achieved by closely spacing the cords so that the cushion can be bent along the row of cords. Thus, these tension cords 220 create a crease line or seam line along the mattress where it may be bent. A folded and bent mattress is shown in FIG. 10. Also, the crease lines or hinges enable other portions of the mattress to easily conform to the shape of a supporting object such as a frame 220 shown in FIG. 11. While an array of tension cords 220 as shown in FIGS. 9-11 has been found suitable for making this fold line or crease line, it is also possible to sew non-stretchable panels or seams through the material from the top to bottom to achieve the same effect. As in the other FIGS., the surface of the mattress is preferably of a stretchable fabric and is maintained a tension by filling the mattress with a plurality of thermoplastic spheres also as described above. Again, this mattress can be shaped to conformed to the outline of the user or the item to be supported.

In order to use the cushion, one merely compresses the exterior surface areas to conform the cushion to the shape of the object or body member to be supported (i.e. arm, elbow, leg, shoulder, etc.). The pellets or spheres easily move around each other as the tension members contract, thus enabling the cushion to be easily and quickly formed to the desired shape. In the event the cushion is extremely compressed in certain areas, such as it exposed to a heavy load, the expanded thermoplastic spheres are capable of being compressed to accommodate the load. Upon removal of the load, the pellets or spheres return to their original spherical shape, although the cushion itself will not return to its original configuration. Should a different configuration or shape be desired for the cushion, the user must again compress or shape the cushion to the desired new configuration.

As one skilled in the art can realize, the present invention is ideally suited for arthritis sufferers, patients recovering from surgery, those suffering from backache, pain or discomfort caused by difficult pregnancies, temporary sprains, sports injuries, broken bones, or the like. One of the advantages of the cushions of this invention is that they can be adjusted to the precise shape for maximum comfort and support of the body member. Therefore, the user is able to completely relax while the body member is supported and this facilitates resting and sleeping much easier than if the body member were rested or being supported upon a conventional pillow or cushion that could not be shaped to exactly meet the user's need.

The size of the overall cushion is not critical to the invention. Sizes can vary from relatively small (i.e. that sufficient for supporting a head, hand or foot), to very large which, for example, can be used in place of a bed mattress for support of the entire body of the user. Although practically any shape can be used, the following have been found to be particularly useful: wedge, tube or cylinder, truncated pyramid, sphere, eggshape, box (six-sided-rectangular or square), and triangular. As noted above, the extreme light weight of the preferred embodiments enable the cushion to be easily handled, moved or shaped by the user.

While it is apparent that the invention herein disclosed is well calculated to fulfill the objects above stated, it will be appreciated that numerous embodiments and modifications may be devised by those skilled in the art, and it is intended that the appended claims cover all such modifications and embodiments as fall within the true spirit and scope of the present invention.

What is claimed is:

1. A lightweight, shapable cushioning apparatus which is easily conformable to a desired configuration for supporting an item comprising:
   exterior surface means of a material stretchable in two directions for forming a desired shape for the apparatus and defining an internal cavity therein; and
   a plurality of lightweight, resilient, solid, expanded rounded thermoplastic particles substantially completely filling said internal cavity, said rounded particles capable of compression, deformation and three-dimensional movement throughout the internal cavity to allow shaping of the apparatus for support of an item, said rounded particles further capable of returning to their rounded shape after the item to be supported is removed from the apparatus; said exterior surface means and rounded particles capable of easily conforming to the desired configuration while also providing softness, lightweight and washability features to the apparatus.

2. The apparatus of claim 1 which further comprises external means for prestressing said exterior surface means.

3. The apparatus of claim 1 wherein said exterior surface means is a natural or synthetic fabric.

4. The apparatus of claim 1 wherein a majority of said rounded particles are spheres having a diameter of between about 1/64 and ½ inch.

5. The apparatus of claim 1 where a portion of said exterior surface means is of a non-stretchable material to assist in holding, guiding or maintaining the shape of the apparatus.

6. The apparatus of claim 1 further comprising means for adjusting the shape of the apparatus.

7. The apparatus of claim 6 wherein one end of the adjusting means is attached to the exterior surface means and wherein another end of the adjusting means passes through said exterior surface means.

8. The apparatus of claim 7 further comprising locking means attachable to said adjusting means for maintaining a predetermined position of said apparatus.

9. The apparatus of claim 8 wherein the adjusting means comprises draw cord means extending through the internal cavity.

10. A lightweight shapable cushioning apparatus which is easily conformable to a desired configuration for supporting an item comprising:
    exterior surface means of a material stretchable in two directions for forming a desired shape for the apparatus and defining an internal cavity therein;
    means for adjusting a dimension of said shape, said adjusting means extending through said internal cavity for forcing one dimension of said exterior surface to any position located between an elongated position and a compressed position, a first end of said adjusting means attached to said surface means with a second end of said adjusting means extending through said exterior surface means to facilitate operation of said adjustment means; and
    a plurality of lightweight, resilient solid, expanded, rounded thermoplastic particles substantially completely filling said internal cavity, said particles capable of compression, deformation and three-dimensional movement throughout the internal cavity without interference from the adjustment means to allow shaping of the apparatus for support of an item, said particles further capable of returning to their rounded shape after the item to be supported is removed from the apparatus; said exterior surface means, adjustment means and particles capable of easily conforming to the desired configuration while also providing softness, lightweight and washability features to the apparatus.

11. The apparatus of claim 10 which further comprises external means for prestressing said exterior surface means.

12. The apparatus of claim 10 wherein said exterior surface means is a natural or synthetic fabric.

13. The apparatus of claim 10 wherein the adjusting means passes through the surface means in at least three locations.

14. The apparatus of claim 10 further comprising locking means attachable to said adjusting means for maintaining a predetermined configuration of said apparatus.

15. The apparatus of claim 10 wherein a majority of said rounded thermoplastic particles are spheres having a diameter of between about 1/64 and ½ inch.

16. A lightweight, shapable cushioning apparatus which is easily conformable to a desired configuration for supporting an item comprising:
    exterior surface means of a flexible, fabric material stretchable in two directions for forming a desired shape for the apparatus and defining an internal cavity therein, a portion of said exterior surface means being of a non-stretchable fabric material to assist in obtaining a desired shape for the apparatus; and
    a plurality of lightweight, resilient, solid expanded, rounded thermoplastic particles substantially completely filling said internal cavity to retain said exterior surface means in the desired shape, said particles capable of reversible compression, deformation and three-dimensional movement throughout the internal cavity without interference to allow shaping of an apparatus for support of an item, said particles further capable of returning to their rounded shape after the item to be supported is removed from the apparatus;

said exterior surface means and rounded particles capable of easily conforming to the desired configuration while also providing softness, lightweight and washability features to the apparatus.

17. The apparatus of claim 16 wherein said rounded particles are spherical and a majority of said particles have a diameter of between about 1/64 and ½ inch.

18. A lightweight, shapable cushioning apparatus which is easily conformable to a desired configuration for supporting an item comprising:

exterior surface means of a flexible, fabric material stretchable in two directions for forming a desired shape for the apparatus and defining an internal cavity therein;

frame means of a substantially rigid material located within the internal cavity to assist in maintaining the desired shape of the apparatus; and a plurality of lightweight, resilient, solid, expanded, rounded thermoplastic particles substantially completely filling said internal cavity to retain said exterior surface means in the desired shape, said rounded particles capable of compression, deformation and three-dimensional movement to allow shaping of the apparatus for support of an item, yet further capable of returning to their rounded shape after the item to be supported is removed from the apparatus.

19. The apparatus of claim 18 wherein a majority of said rounded particles are spheres having a diameter of between about 1/64 and ½ inch.

20. The apparatus of claim 19 which further comprises external means for prestressing said exterior surface means.

21. A lightweight, shapable cushioning apparatus which is easily conformable to a desired configuration for supporting an item comprising:

exterior surface means of a material stretchable in two directions for forming a desired shape for the apparatus and defining an internal cavity therein;

means for adjusting a dimension of said shape, said adjusting means extending through said internal cavity for forcing one dimension of said exterior surface to any position located between an elongated position and a compressed position, a first end of said adjusting means attached to said surface means with a second end of said adjusting means extending through said exterior surface means in a more than one location to facilitate operation of said adjustment means;

external means for prestressing said exterior surface means; and a plurality of lightweight, resilient, solid, expanded rounded thermoplastic particles substantially filling said internal cavity, said particles capable of compression, deformation and three-dimensional movement through the internal cavity without interference from the adjustment means to allow shaping of the apparatus for support of an item, said particles further capable of returning to their rounded shape after the item to be supported is removed from the apparatus; said exterior surface means, adjustment means and particles capable of easily conforming to the desired configuration while also providing softness, lightweight and washability features to the apparatus.

22. The apparatus of claim 21 wherein said exterior surface means is a natural or synthetic fabric and wherein the adjusting means passes through the surface means in at least three locations.

23. The apparatus of claim 21 wherein a majority of said rounded particles are spheres having a diameter of between about 1/64 and ½ inch.

* * * * *